(12) United States Patent
Potyrailo et al.

(10) Patent No.: US 6,671,631 B2
(45) Date of Patent: Dec. 30, 2003

(54) SYSTEMS AND METHODS FOR ANALYZING VISCOELASTIC PROPERTIES OF COMBINATORIAL LIBRARIES OF MATERIALS

(75) Inventors: Radislav Alexandrovich Potyrailo, Niskayuna, NY (US); William Guy Morris, Rexford, NY (US); Ronald Eugene Shaffer, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 58 days.

(21) Appl. No.: 10/038,455

(22) Filed: Jan. 4, 2002

(65) Prior Publication Data

US 2003/0130804 A1 Jul. 10, 2003

(51) Int. Cl.$^7$ .......................... G01N 31/00; G06F 19/00
(52) U.S. Cl. .......................... 702/30; 702/22; 324/71.1; 324/715; 436/2; 73/23.2; 374/10
(58) Field of Search .................. 702/30, 22; 324/71.1, 324/715; 436/2; 73/23.2; 374/10

(56) References Cited

U.S. PATENT DOCUMENTS

| | | | |
|---|---|---|---|
| 4,312,228 A | 1/1982 | Wohltjen | 73/597 |
| 4,963,815 A | 10/1990 | Hafeman | 324/715 |
| 4,969,359 A | 11/1990 | Mikkor | 73/517 |
| 5,130,257 A | 7/1992 | Baer et al. | 436/151 |
| 5,317,252 A * | 5/1994 | Kranbuehl | 324/71.1 |
| 5,445,008 A | 8/1995 | Wachter et al. | 73/24.06 |
| 5,451,371 A | 9/1995 | Zanini-Fisher et al. | 422/51 |
| 5,494,639 A | 2/1996 | Grzegorzewski | 422/82.01 |
| 5,563,341 A | 10/1996 | Fenner et al. | 73/335.11 |
| 5,719,324 A | 2/1998 | Thundat et al. | 73/24.01 |
| 6,016,686 A | 1/2000 | Thundat | 73/23.2 |
| 6,079,873 A | 6/2000 | Cavicchi et al. | 374/10 |
| 6,096,559 A | 8/2000 | Thundat et al. | 436/147 |
| 6,106,149 A | 8/2000 | Smith | 374/31 |
| 6,126,311 A | 10/2000 | Schuh | 374/21 |
| 6,157,009 A | 12/2000 | Fauske et al. | 219/497 |
| 6,167,748 B1 | 1/2001 | Britton, Jr. et al. | 73/24.06 |
| 6,182,499 B1 | 2/2001 | McFarland et al. | 73/24.06 |
| 6,269,685 B1 | 8/2001 | Oden | 73/54.23 |
| 6,289,717 B1 | 9/2001 | Thundat et al. | 73/23.2 |
| 6,553,318 B2 * | 4/2003 | Mansky | 702/22 |
| 2002/0173040 A1 * | 11/2002 | Potyrailo et al. | 436/2 |

FOREIGN PATENT DOCUMENTS

WO    WO 00/36410    6/2000

OTHER PUBLICATIONS

Ballantine D.S., Jr., White, R.M.; Martin, S.J.; Ricco, A.J.; Frye, G.C.; Zellers, E.T.; Wohltjen, H. *Acoustic Wave Sensors: Theory, Design, and Physico–Chemical Applications*; Academic Press: San Diego, CA, 1997, Chapter 4, pp. 150–212.

Diefenderfer, A. J. *Principles of Electronic Instrumentation*; Saunders College Publishing: Philadelphia, PA, 1979, pp. 61 and 91–97.

Booksh, K. S.; Kowalski, B. R., Theory of analytical chemistry, *Anal. Chem.* 1994, 66, 782A–791A.

Bro, R.; Workman, J. J., Jr.; Mobley, P. R.; Kowalski, B. R., Review of chemometrics applied to spectroscopy: 1985–95, Part 3—Multi–way analysis, *Appl. Spectrose. Rev.* 1997, 32, 237–261.

* cited by examiner

*Primary Examiner*—John Barlow
*Assistant Examiner*—Tung Lau
(74) *Attorney, Agent, or Firm*—Christopher L. Bernard, PLLC

(57) ABSTRACT

Systems and methods for analyzing a viscoelastic property of a combinatorial library of materials including a plurality of full bridge devices operable for measuring a temperature-modulated elongation property of each of a plurality of combinatorial materials, wherein each of the plurality of full bridge devices comprises a plurality of strain gauges operable for measuring a temperature-modulated elongation property of each of the plurality of combinatorial materials, and wherein each of the plurality of combinatorial materials is disposed on a surface of the plurality of full bridge devices. The systems and methods also including an algorithm disposed within a computer, the algorithm operable for equating the temperature-modulated elongation property of the combinatorial materials with a thermal property of the combinatorial materials.

25 Claims, 9 Drawing Sheets

SYSTEMS AND METHODS FOR ANALYZING VISCOELASTIC PROPERTIES OF COMBINATORIAL LIBRARIES OF MATERIALS

BACKGROUND OF THE INVENTION

The present invention relates generally to systems and methods for analyzing the viscoelastic properties of combinatorial libraries of materials. More specifically, the present invention relates to systems and methods for analyzing the thermal properties of libraries of polymers and polymer films using an array of full bridge devices. The systems and methods of the present invention may also be used to analyze such properties as vapor sorption, chemical resistance, weatherability, and oxidative stability.

Typically, the viscoelastic properties of materials, such as polymers and polymer films, have been analyzed using devices such as acoustic wave devices, micro-hotplates, micromechanical calorimetric sensors, and shear/stress sensors. For example, acoustic wave devices have been used to measure the glass transition temperature and melting temperature of materials. Micro-hotplates have been used as micron-scale differential scanning calorimeters on a chip. Micromechanical calorimetric sensors have been used to detect thermal changes in test samples containing biomolecules undergoing chemical and biochemical reactions. Other sensor devices have been arranged in a standard combinatorial array configuration.

U.S. Pat. No. 4,312,228 discloses an acoustic wave sensor and methods for monitoring predetermined parameters of polymers including generating a surface acoustic wave in a piezoelectric material element and contacting a thin layer of the polymer with the surface through which the acoustic wave travels. The thin polymer layer is subjected to variations in environment thereby modifying the predetermined parameter of the polymer and changing the velocity of acoustic waves in and/or a dielectric property of the polymer, thus altering the frequency, amplitude, and/or phase of the surface acoustic wave. These alterations may be measured and related to glass transition temperature, the rate of solvent evaporation from the polymer, the photo-crosslinking characteristics of the polymer, and the crystalline transition characteristics of the polymer.

U.S. Pat. No. 6,079,873 discloses a differential scanning microcalorimeter produced on a silicon chip that enables microscopic scanning calorimetry measurements of small material samples and thin films. The microcalorimeter includes a reference zone and a sample zone. An integrated polysilicon heater provides heat to each zone and a thermopile including a succession of thermocouple junctions generates a voltage representing the temperature difference between the reference zone and the sample zone. Temperature differences between the zones provide information about the chemical reactions and phase transitions which occur in a sample placed in the sample zone.

U.S. Pat. No. 5,451,371 discloses a non-scanning, constant temperature microcalorimeter device. The device is built on a silicon base which is etched, leaving a frame of silicon supporting two polysilicon platforms. A catalyst is disposed on one platform to sense the presence of hydrocarbons. Platinum resistors on each platform serve as heaters and thermometers.

U.S. Pat. No. 6,096,559 discloses a calorimeter sensor apparatus using microcantilevered spring elements for detecting thermodynamic changes within a material sample containing biomolecules that undergo chemical and biochemical reactions. The spring elements each include a bimaterial layer of chemicals disposed on a coated region of at least one surface of the microcantilever. The chemicals generate a differential thermal stress across the surface upon reaction of the chemicals with an analyte or biomolecules within the sample due to the heat of the resulting reactions. The thermal stress experienced by the spring element creates a mechanical bending of the microcantilever. Deflections of the microcantilever may be detected by a variety of detection techniques.

U.S. Pat. No. 5,719,324 discloses a piezoelectric transducer that is fabricated with a cantilever having a spring element which is treated with a chemical having an affinity for a specific vapor phase chemical. An oscillator means maintains a resonant vibrational frequency during the detection of the chemical, with changes in resonant vibrational frequency indicating amounts of the targeted chemical present in the monitored atmosphere.

U.S. Pat. No. 5,445,008 discloses a mass microsensor that is also fabricated with a microcantilever having a material which absorbs a targeted chemical from the monitored atmosphere. Oscillation is induced using a piezoelectric transducer and the resonant frequency of the microcantilever is analyzed to detect amounts of the targeted chemical present in the monitored atmosphere. U.S. Pat. No. 5,475,318 discloses a microprobe including a microcantilever, a base, a probe tip projecting from the base, and a heating element that may be used to probe the material to be investigated.

U.S. Pat. No. 4,963,815 discloses a device and a method for determining an analyte by measuring a redox potential-modulated photoinducing electrical signal from an electrically conducting layer of a semiconductor device.

U.S. Pat. No. 6,106,149 discloses a mass and heat flow measurement sensor including a microresonator, such as a quartz crystal microbalance (QCM), a heat flow sensor, such as an isothermal heat conduction calorimeter, and a heat sink thermally coupled to the heat flow sensor. The microresonator may be used to measure changes in mass of a material sample at its surface and the heat flow sensor, which is thermally coupled to the microresonator, may be used to measure heat flow from the material sample to the heat sink.

U.S. Pat. No. 6,157,009 discloses a reactive screening tool, such as a calorimeter apparatus, having a low test cell-to-test sample thermal mass ratio so as to minimize heat sink effects on the test sample during chemical reaction. A heater control algorithm includes a calibration stage during which the heater is set to the predetermined test conditions and a test stage during which the heater controls the test conditions in a ramping mode and in an adiabatic mode. The reactive screening tool may also include a foam detector for detecting the presence of foam in the test sample.

U.S. Pat. No. 5,563,341 discloses a vapor pressure sensor including a substrate having a body with first and second parallel planar surfaces. A hole is formed in the body and extends through and between the first and second surfaces. A beam disposed within the hole in the body is formed as a cantilever. A vapor absorbing polyimide coating of substantially uniform thickness is disposed on the surface of the beam in full shear restraint. A strain measuring device forms a portion of a bridge carried by the substrate and measures shear forces exerted on the beam by the vapor absorbing coating.

U.S. Pat. No. 4,969,359 discloses a silicon accelerometer responsive to three (3) orthogonal force components. Three rectangular beams or cantilevers are formed, each having vertical sidewalls lying in crystalline planes orthogonal to one another.

U.S. Pat. No. 6,126,311 discloses a dew point sensor using micro-electromechanical systems (MEMS) including a microcantilevered beam formed on a substrate. A cooling device and a temperature sensor are in thermal communication with the microcantilevered beam and a control circuit operable for controlling and monitoring its resonance. The dew point is determined by identifying the temperature of the microcantilevered beam when its resonance or vibratory mode changes due to a change in mass caused by the formation of dew on the microcantilevered beam.

U.S. Pat. No. 6,016,686 discloses a micromechanical microcantilever potentiometric sensor used for detecting and measuring predetermined physical and chemical parameters in a material sample. A spring element includes a region coated with at least one chemical coating that accumulates a surface charge in response to hydrogen ions, redox potential, or ion concentrations in the material sample being monitored. Differing surface charges on opposing surfaces create a mechanical stress and a deformation of the spring element. A multitude of detection methods may be used to measure the deflection of the spring element and the degree of deflection may be correlated with the physical or chemical parameter of interest.

U.S. Pat. No. 6,269,685 discloses a method for the measurement of the viscosity of a fluid that uses a micromachined cantilever mounted on a moveable base. As the base is rastered while in contact with the fluid, the deflection of the cantilever is measured and the viscosity of the fluid is determined by comparison with standards. U.S. Pat. No. 5,130,257 discloses a viscosity sensor fabricated using a surface transverse wave device. Similarly, U.S. Pat. No. 5,494,639 discloses a disposable biosensor that uses a vibrating member disposed beneath a cell operable for measuring blood coagulation time as a function of viscosity.

U.S. Pat. No. 6,167,748 discloses a multi-element sensor array with common-mode cancellation and a multi-element apparatus for detecting the presence of at least one chemical, biological, or physical component in a monitored area. The array includes a capacitive transducer having at least one cantilever spring element coated with a chemical having an affinity for the component to be detected, a pick-up plate, and detection means for measuring the variation in capacitance between the cantilever spring element and the pick-up plate, forming a measurement channel signal.

U.S. Pat. No. 6,289,717 discloses a micromechanical antibody sensor using a microcantilevered spring element having a detector molecule coating, such as an antibody or antigen coating. A material sample containing a target molecule or substrate is introduced to the coating. The spring element measurably bends in response to the stress induced by the binding that occurs between the detector molecules and the target molecules.

Such systems and methods, although marginally useful, suffer from several important limitations when used to analyze the viscoelastic properties of combinatorial libraries of materials, such as libraries of polymers and polymer films. The operation of an array of sensors in the screening of combinatorial libraries of materials is typically unacceptably slow. Measurements are typically performed in a serial fashion and the screening of as few as 100 combinatorial materials may take in excess of 90 minutes. The electronics used to operate such arrays of sensors are also complex and expensive. For example, a lock-in amplifier is typically required. Finally, the use of shear/stress sensors as true microcalorimeters in the analysis of the thermal properties of combinatorial libraries of materials is limited because such sensors typically do not have individual heaters associated with them. Thus, the use of such sensors in the thermal analysis of combinatorial libraries materials requires the use of separate heaters and temperature sensors, and a complete modification of the sensor elements. Thus, what is needed are systems and methods that provide improved capabilities for the analysis of the thermal properties of combinatorial libraries of materials, such as libraries of polymers and polymer films. What is needed are systems and methods that allow for the simultaneous and continuous measurement, with high sensitivity and accuracy, of the viscoelastic changes in a plurality of low volume material samples, such as those generated in combinatorial chemistry experiments. Furthermore, due to the large number of samples involved in a typical combinatorial chemistry experiment, automated computational methods for the detection of outliers and the determination of viscoelastic properties are needed.

BRIEF SUMMARY OF THE INVENTION

The present invention provides systems and methods having improved capabilities for the analysis of the viscoelastic properties of combinatorial libraries of materials, such as libraries of polymers and polymer films. These systems and methods include the use of an array of miniaturized shear/stress devices, or full bridge devices, that operate in parallel, providing simultaneous and continuous responses. The sensor data may be read electronically and is used an input for multivariate statistical algorithms providing data extraction and compression for automated outlier detection and improved analysis.

In one embodiment, a system for analyzing a viscoelastic property of combinatorial materials includes a plurality of full bridge devices operable for measuring an environment-modulated elongation property of the combinatorial materials, wherein each of the plurality of full bridge devices comprises a plurality of strain gauges operable for measuring an environment-modulated elongation property of the combinatorial materials, and wherein each combinatorial material is disposed on a surface of the plurality of full bridge devices. The system also includes a mathematical algorithm disposed within a computer, the mathematical algorithm operable for equating the environment-modulated elongation property of the combinatorial materials with a viscoelastic property of the combinatorial materials.

In another embodiment, a method for analyzing a viscoelastic property of combinatorial materials includes providing a plurality of full bridge devices operable for measuring an environment-modulated elongation property of the combinatorial materials, wherein each of the plurality of full bridge devices comprises a plurality of strain gauges operable for measuring the environment-modulated elongation property of the combinatorial materials, disposing the combinatorial materials on a surface of the plurality of full bridge devices, and measuring the environment-modulated elongation property of each combinatorial material. The method also includes providing a mathematical algorithm operable for equating the environment-modulated elongation property of the combinatorial materials with a viscoelastic property of the combinatorial materials and equating the environment-modulated elongation property of the combinatorial materials with a viscoelastic property of the combinatorial materials.

Advantageously, the present invention provides systems and methods that use a plurality of strain gauges and the temperature-modulated elongation properties of a polymer or polymer film to characterize the thermal properties of the polymer or polymer film. These systems and methods are capable of measuring the thermal properties of any combinatorial material that may be deposited onto a substrate and that experiences stress when a member held in full shear restraint is subjected to varying thermal or other conditions. These systems and methods allow for the mass-independent characterization of polymers and polymer films using a miniaturized, inexpensive, mass-produced device. Finally, the systems and methods of the present invention allow for the simultaneous and continuous measurement of signals produced by a plurality of individual devices, allowing for the simultaneous and continuous analysis of data using multivariate statistical data analysis techniques and visualization algorithms.

DETAILED DESCRIPTION OF THE INVENTION

Figure 1:
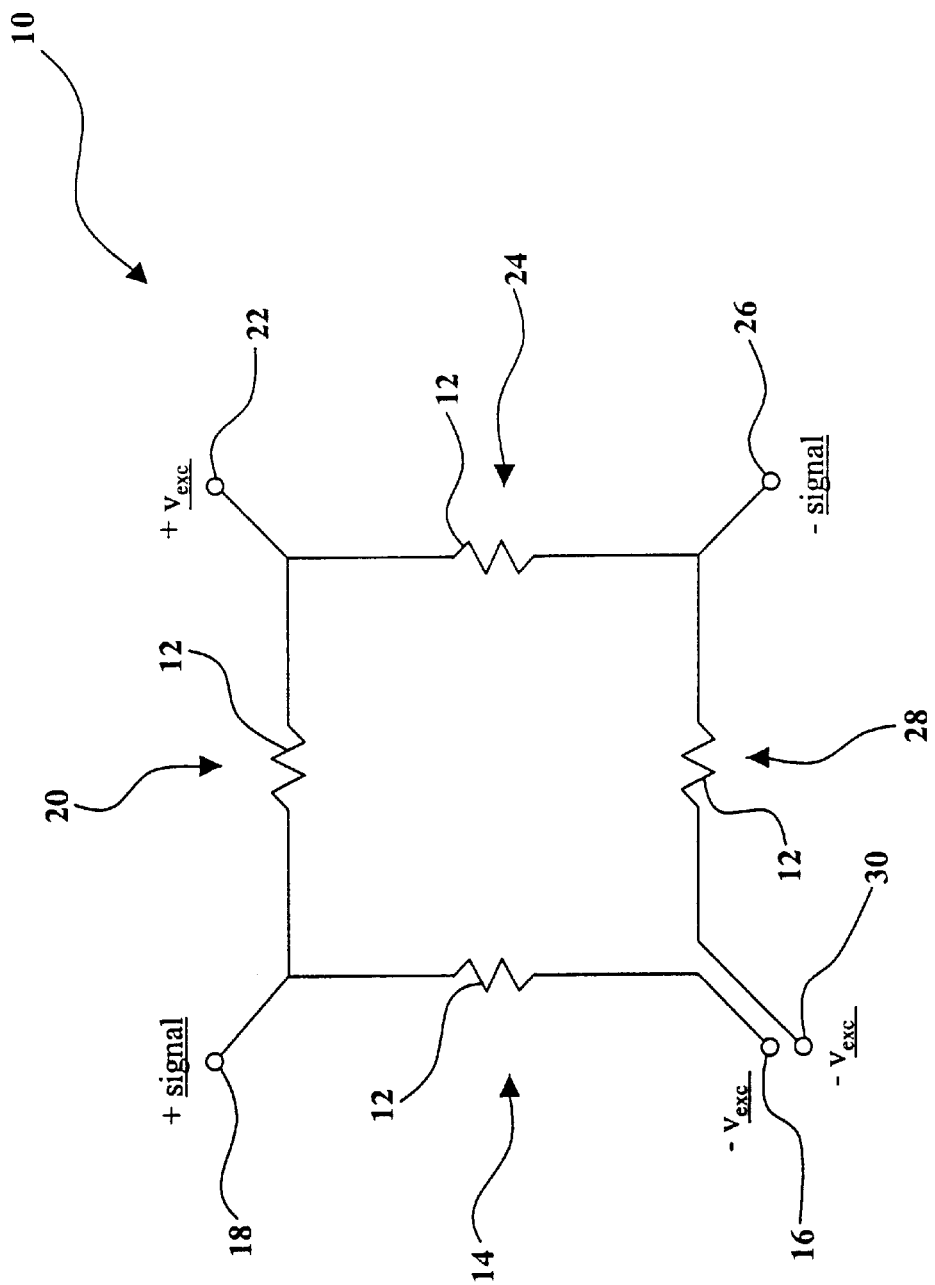
FIG. 1 is a circuit diagram of one embodiment of a full bridge device operable for analyzing the viscoelastic properties of combinatorial libraries of materials, such as libraries of polymers and polymer films.

Referring to FIG. 1, in one embodiment, a full bridge device 10 operable for analyzing the viscoelastic properties, such as thermal properties, of combinatorial libraries of materials is operable for measuring the environment-modulated elongation properties, such as temperature-modulated elongation properties, of a polymer or polymer film deposited onto a surface of the full bridge device 10 and relating these measurements to the viscoelastic properties, such as thermal properties, of the polymer or polymer film. This temperature-modulated elongation may also be referred to as thermal expansion or thermal dilatometry. The temperature-modulated elongation properties are measured by a plurality of strain gauges 12 for the purpose of measuring such thermal and viscoelastic properties as glass transition temperature, vapor sorption, chemical resistance, weatherability, and oxidative stability. The strain gauges 12 each include a small diameter wire or etched metal foil fixedly attached to a substrate or baking material. As strain in the wire or metal foil increases, the electrical resistance of the wire or metal foil increases. This change in electrical resistance may be observed and measured. In the embodiment shown, the full bridge device 10 includes four (4) strain gauges 12, each strain gauge 12 forming an arm of the bridge. The first arm of the bridge 14 is connected to a negative voltage ($-V_{exc}$) terminal 16 at one end and a positive signal (+Signal) terminal 18 at the other end. The second arm of the bridge 20 is connected to the +Signal terminal 18 at one end and a positive voltage ($+V_{exc}$) terminal 22 at the other end. The third arm of the bridge 24 is connected to the $+V_{exc}$ terminal 22 at one end and a negative signal (−Signal) terminal 26 at the other end. The fourth arm of the bridge 28 is connected to the −Signal terminal 26 at one end and another negative voltage ($-V_{exc}$) terminal 30 at the other end. This full bridge configuration, as is well known to those of ordinary skill in the art, may achieve enhanced temperature compensation as a portion of the temperature effects are cancelled out by the bridge itself. As is also well known to those of ordinary skill in the art, such devices provide mass-independent measurements.

In general, the full bridge device 10 of the present invention, i.e. the viscoelastic property sensor, is arranged, for example, as a micro-electromechanical system (MEMS) having control circuitry, which is preferably integrated, for operating the MEMS. The viscoelastic property sensor includes a temperature sensor in thermal communication with the MEMS, thereby enabling a more accurate measurement of the temperature at which a change in the viscoelastic properties takes place. The change in the viscoelastic properties is detected as the change in the strain state of the MEMS device.

The combinatorial library of materials may be exposed to environmental conditions and variations such as electromagnetic radiation in the spectral range of, for example, about 50 Angstroms–500 millimeters, about 150 nanometers–2500 nanometers, and about 250 nanometers–1000 nanometers. The electromagnetic radiation power density at the surface may be from, for example, about 1 nanoWatt per square centimeter–100 GigoWatts per square centimeter, about 100 nanoWatts per square centimeter–100 MegaWatts per square centimeter, and about 100 microWatts per square centimeter–10 MegaWatts per square centimeter. The temperature may be from, for example, about 24 K–2273 K, about 203 K–1273 K, and about 223 K–873 K. The vapor partial pressure may be from, for example, about 0.0001 Atmosphere–100 Atmosphere, about 0.001 Atmosphere–10 Atmosphere, and about 0.01 Atmosphere–5 Atmosphere. The fluid concentration may be from, for example, about 1 part per billion–100 percent, about 1 part per million–100 percent, and about 1 part per thousand–100 percent. Finally, the combinatorial material amount may be from, for example, about 1 femtogram–100 microgram, about 1 picogram–10 microgram, and about 1 nanogram–1 microgram.

The response of a plurality of full bridge devices 10 is preferably analyzed using multivariate statistical data analysis techniques. Each full bridge device 10 is a first-order instrument that generates a matrix of data per test sample (including elapsed analysis time related to changing temperature and device output). Such a first-order instrument may be modulated by another parameter, such as the heating/cooling rate during multiple cycles, the addition of extra combinatorial material to the full bridge device 10 after a given number of cycles, and the like. While the complexity of the data analysis increases with increasing data dimensionality, the accuracy, precision, and merit of the measurement of the thermal properties of a combinatorial material also increases.

The response of the plurality of full bridge devices 10 may be analyzed using, for example, a visualization algorithm. A visualization algorithm is an approach to data analysis that stresses a penetrating look at the data. Graphing and fitting comprise the two components of visualizing the structure of a data set. Visualization algorithms are mathematical techniques that perform the graphing or fitting of data. For multivariate data sets, techniques that compress and extract data are particularly useful. For example, PCA finds linear combinations of the original variables to construct a new, lower dimensional coordinate system for the graphing and plotting of data. Non-linear mapping (NLM) provides another visualization tool for graphing multidimensional data sets. NLM is based upon a point mapping of the original data to a lower dimensional space such that the inherent structure of the data is approximately preserved under the mapping. Other techniques in the literature for multivariate visualization of data include multidimensional scaling, correspondence factor analysis, and Kohonen's self-organizing map neural network. Among these choices, PCA is preferred in this application because of its signal-averaging benefits and its ability to uncover anomalous patterns in the data structure (e.g., an outlier). However, the other approaches, described above, could be used by those of ordinary skill in the art.

Working Example

An array of full bridge devices 10 was constructed for the analysis of the thermal properties of polymers and polymer films. Data acquisition was performed using a suitable program written in LabVIEW (National Instruments, Austin, Tex.). Various polymers were dissolved in chloroform at different concentrations ranging from about 0.5 wt % to about 10 wt %. Small amounts of the polymer solutions were deposited onto the full bridge devices 10 and the solvent was allowed to evaporate in air at about room temperature. Amounts of the deposited solutions ranged from about 0.5 microliters to about 10 microliters. The array of full bridge devices 10, with the deposited polymer films, was disposed within a temperature-controlled chamber. A suitable temperature-controlled chamber may include, for example, a gas chromatographic oven. The temperature of the chamber was ramped with a ramp rate of about 5 degrees C. to about 20 degrees C. per minute. Measurements were simultaneously and continuously performed using all channels of the array of full bridge devices 10.

Figure 2:
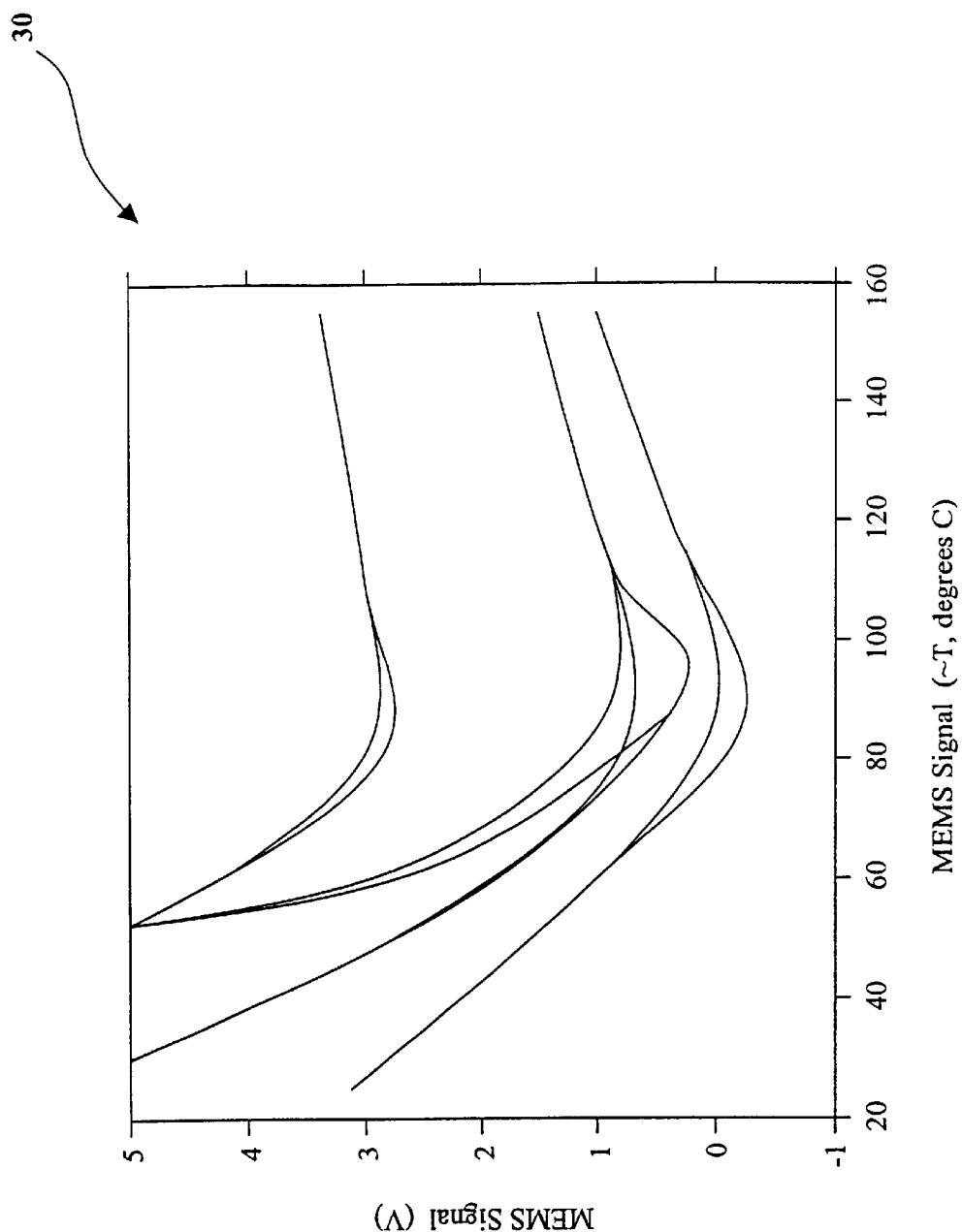
FIG. 2 is a graph illustrating the simultaneous and continuous analysis of the glass transition temperature of polymers deposited onto an array of four (4) full bridge devices of the present invention.
Figure 3:
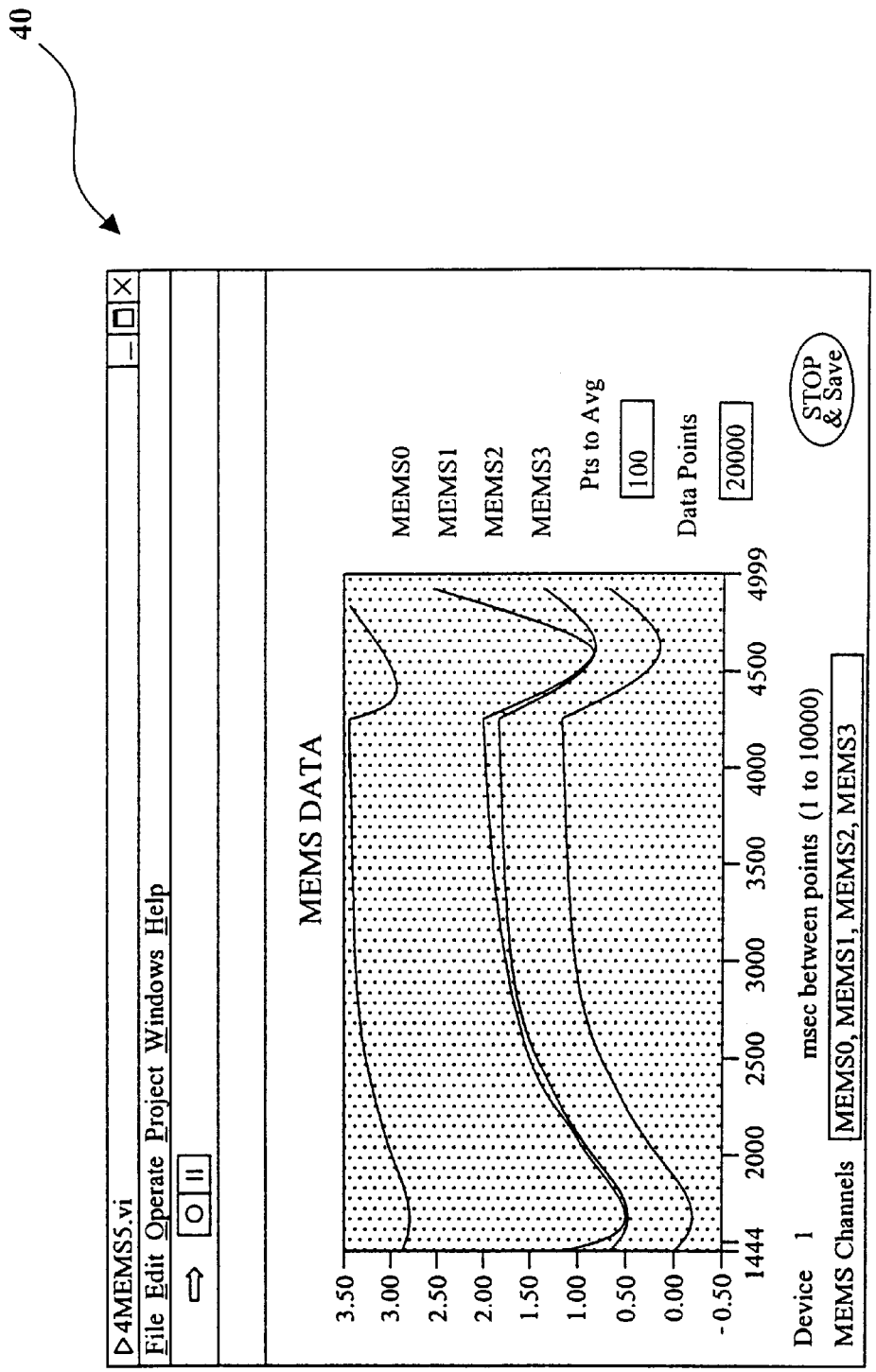
FIG. 3 is an example of one embodiment of a display of the data acquisition system of the present invention, illustrating the simultaneous and continuous response of the individual full bridge devices of the present invention to a change in the elongation properties of polystyrene films upon heating and cooling.
Figure 4:
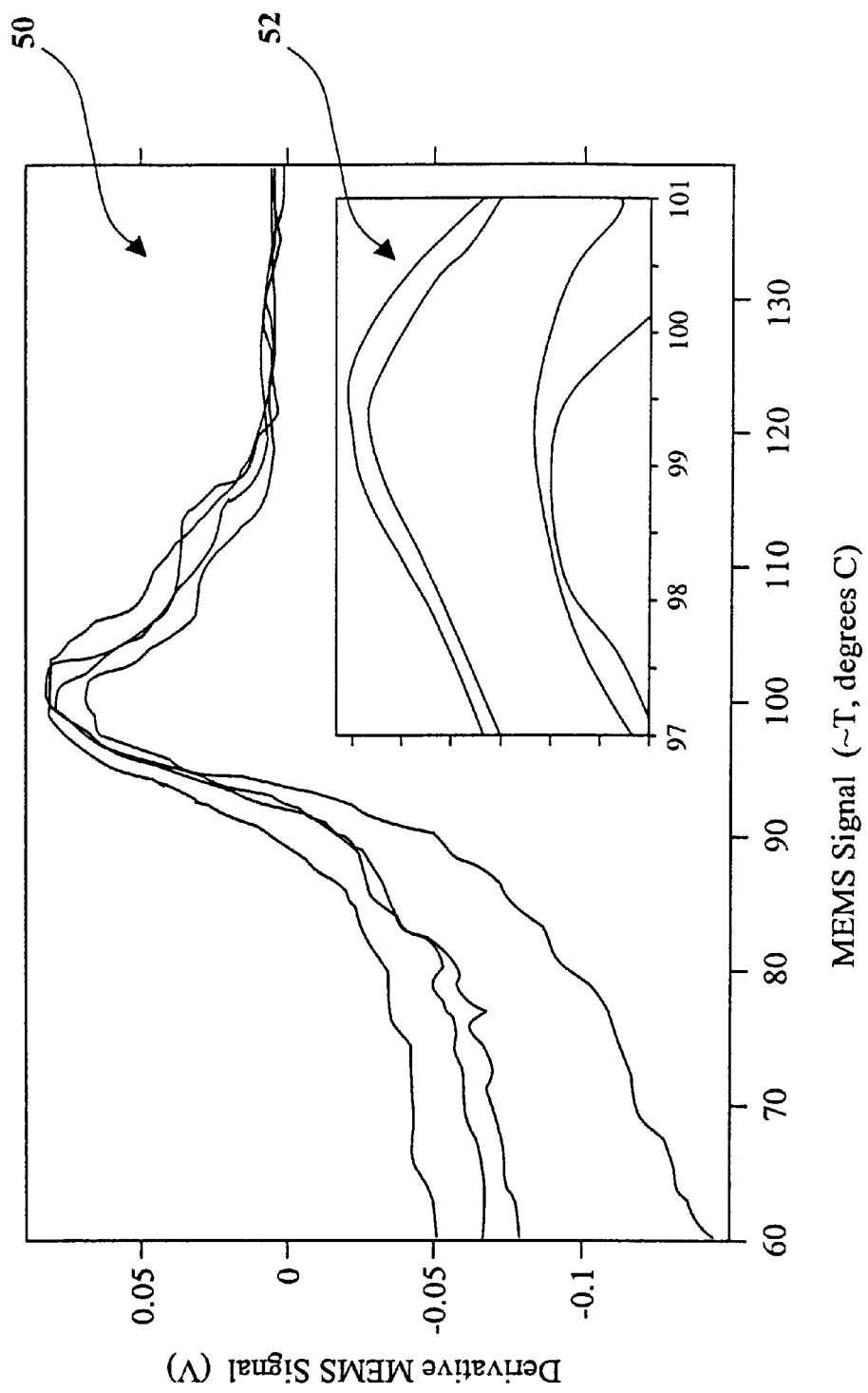
FIG. 4 is a graph illustrating the results of signal analysis for the accurate, precise determination of the glass transition temperatures of polymers deposited onto the full bridge devices of the present invention.
Figure 5:
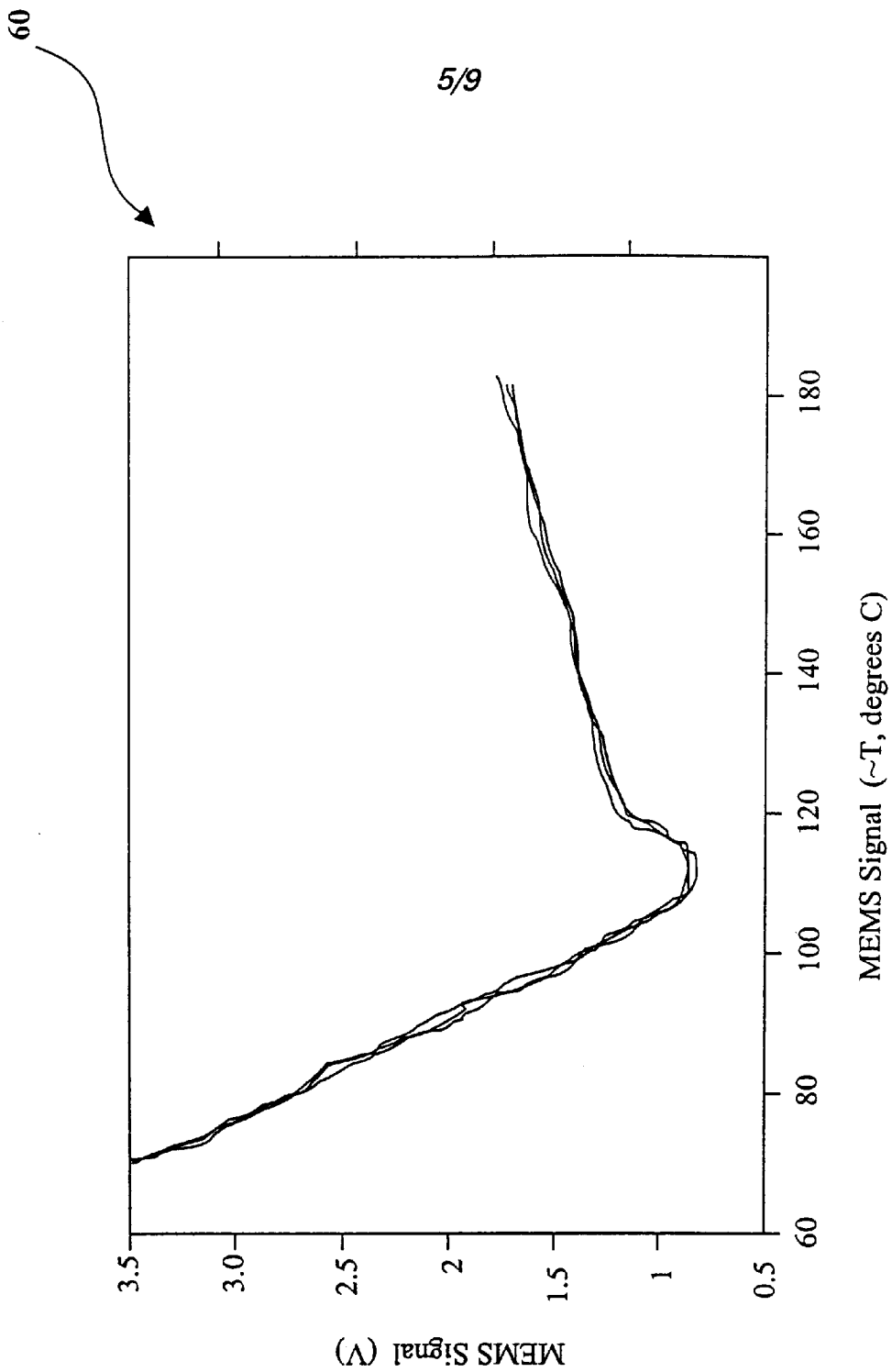
FIG. 5 is a graph illustrating the traces of a given full bridge device of the present invention upon multiple heating cycles of a poly(methyl methacrylate) (PMMA) film.
Figure 6:
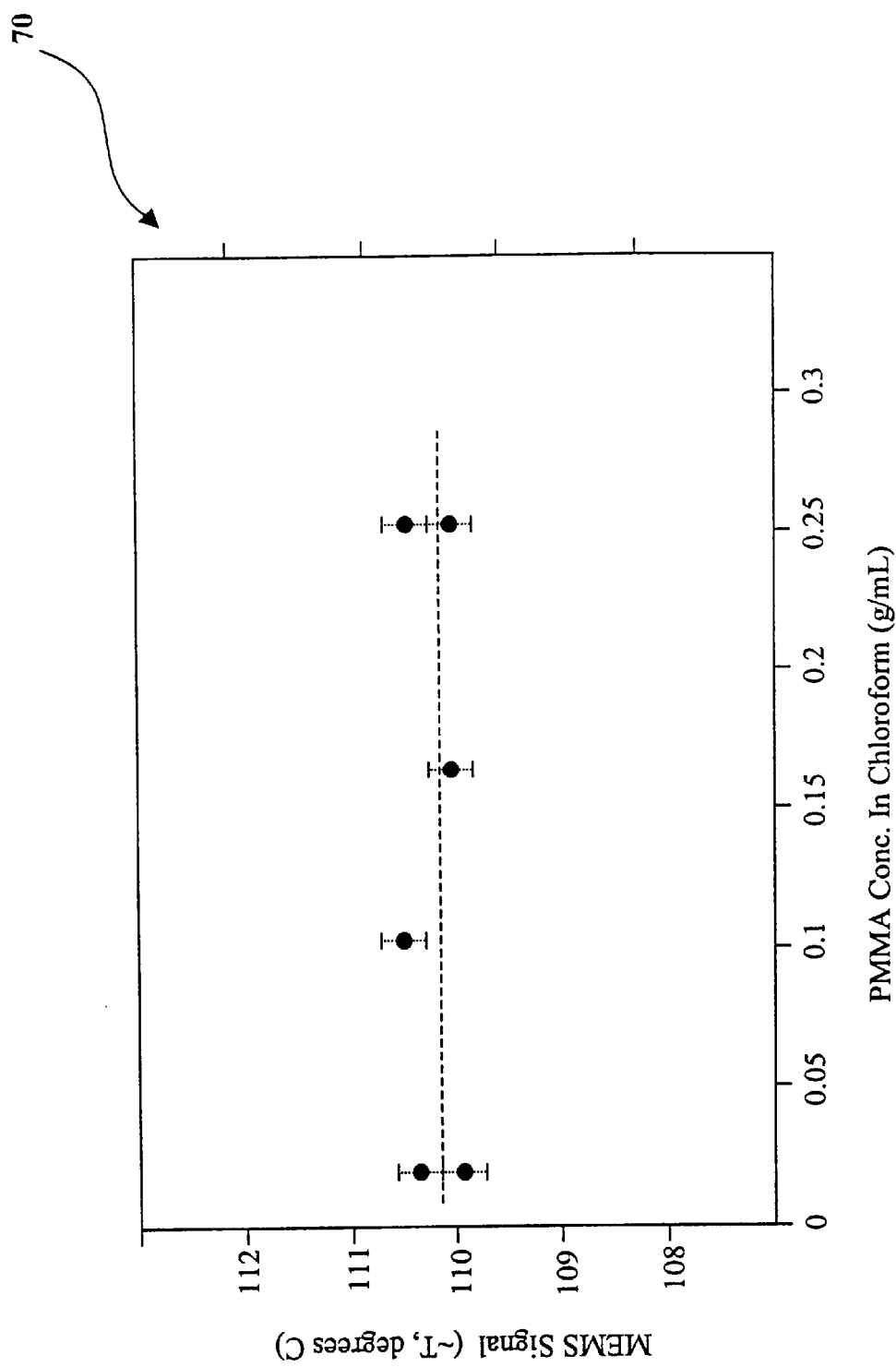
FIG. 6 is a plot illustrating that the response of the full bridge devices of the present invention is independent of the mass of the deposited combinatorial library of materials.
Figure 7:
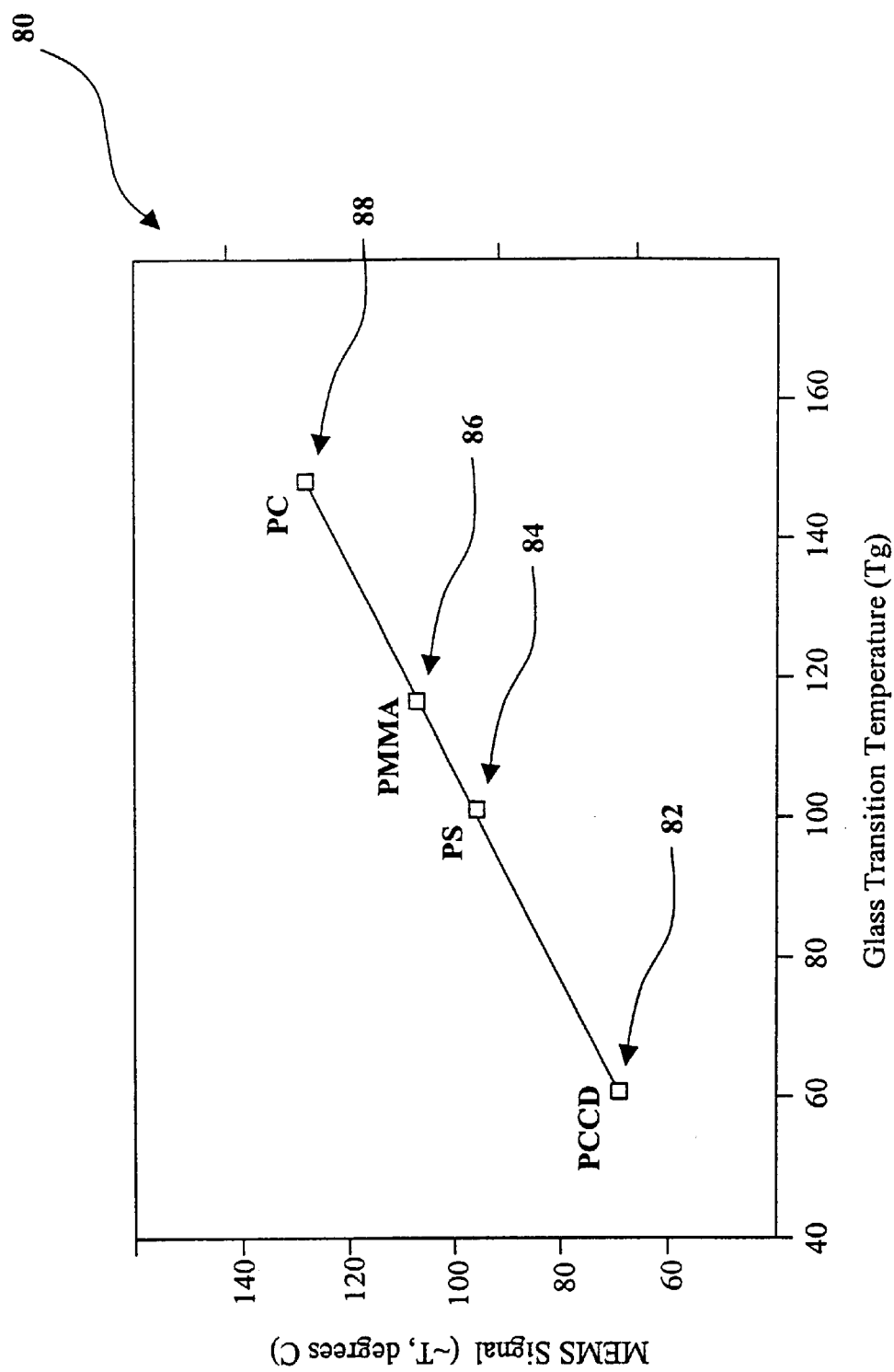
FIG. 7 is a graph illustrating the calibration results for the determination of the glass transition temperature of different polymers using the full bridge devices of the present invention.

The graph 30 of FIG. 2 illustrates the simultaneous and continuous analysis of the glass transition temperature of polymers (polystyrene) deposited onto an array of four (4) full bridge devices 10 (FIG. 1) (MEMS0, MEMS1, MEMS2, and MEMS3). FIG. 3 is an exemplary display 40 of the data acquisition system, illustrating the simultaneous and continuous response of individual full bridge devices 10 (FIG. 1) in the array to a change in the elongation properties of polystyrene films upon the heating and cooling of the array of full bridge devices 10. The graph 50 of FIG. 4 illustrates the results of signal analysis for the accurate, precise determination of the glass transition temperatures of polymers deposited onto each full bridge device 10 (FIG. 1) of the array. The inset graph 52 is an expanded view of the peak at about 100 degrees C. The polymer in all channels of the array of full bridge devices 10 was polystyrene. The reproducibility of device performance was evaluated by running multiple analyses. The graph 60 of FIG. 5 illustrates the traces of a given full bridge device 10 (FIG. 1) upon multiple heating cycles of a poly(methyl methacrylate) (PMMA) film. The dependence of the device response in the determination of glass transition temperature was evaluated using solutions of different polymers dissolved in chloroform at different concentrations. The plot 70 of FIG. 6 illustrates that the response of the full bridge devices 10 (FIG. 1) is independent of the mass of the deposited combinatorial material. The graph 80 of FIG. 7 illustrates the calibration results for the determination of the glass transition temperature of different polymers, including poly(1,4-cyclohexylenedimethylene-1,4-cyclohexanedicarboxylate) (PCCD) 82, polystyrene (PS) 84, PMMA 86, and polycarbonate (PC) 88.

Figure 8:
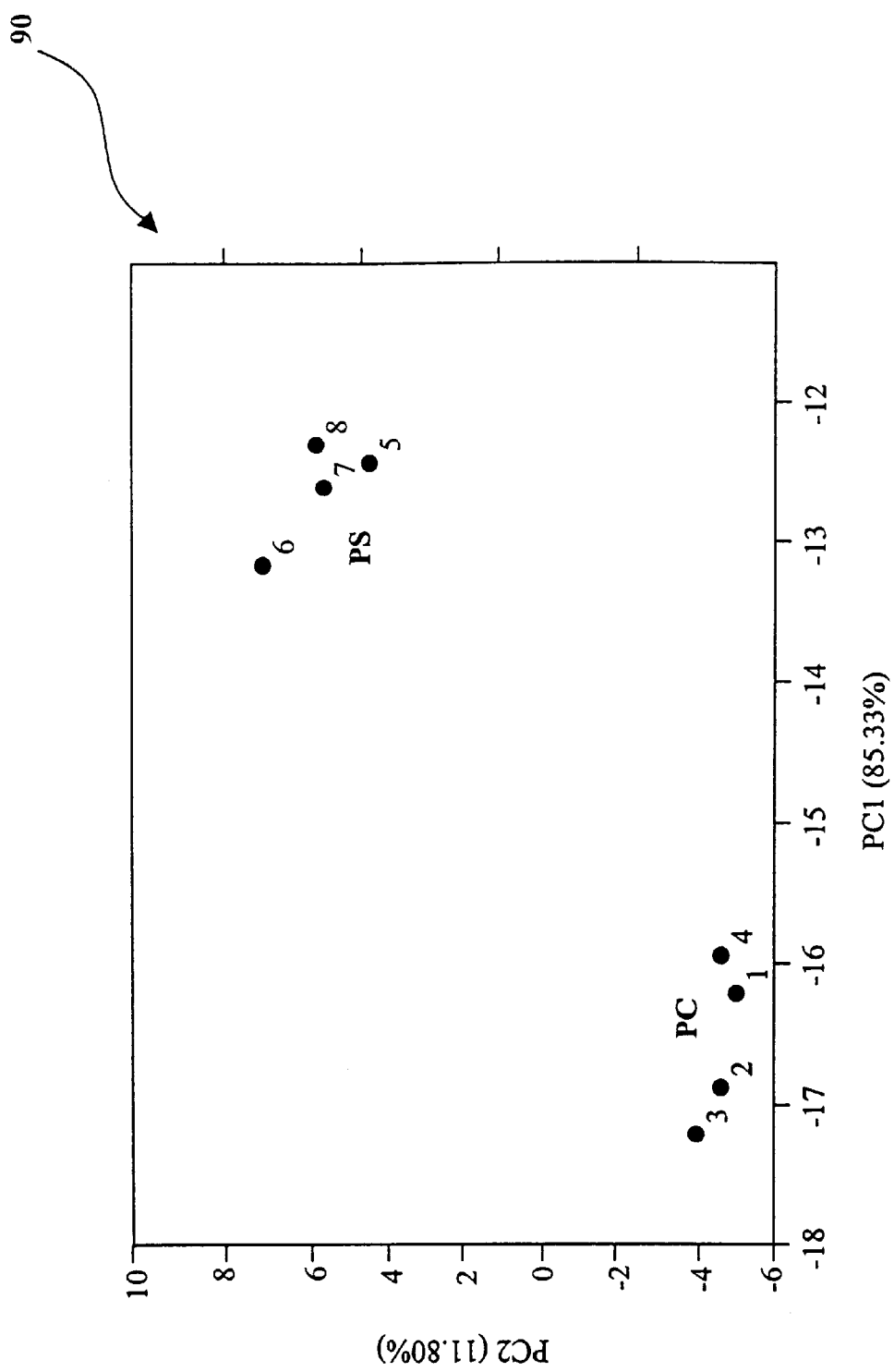
FIG. 8 is a plot illustrating the results of a Principal Components Analysis (PCA) scores plot for two polymer films evaluated in the four-channel array of full bridge devices of the present invention.
Figure 9:
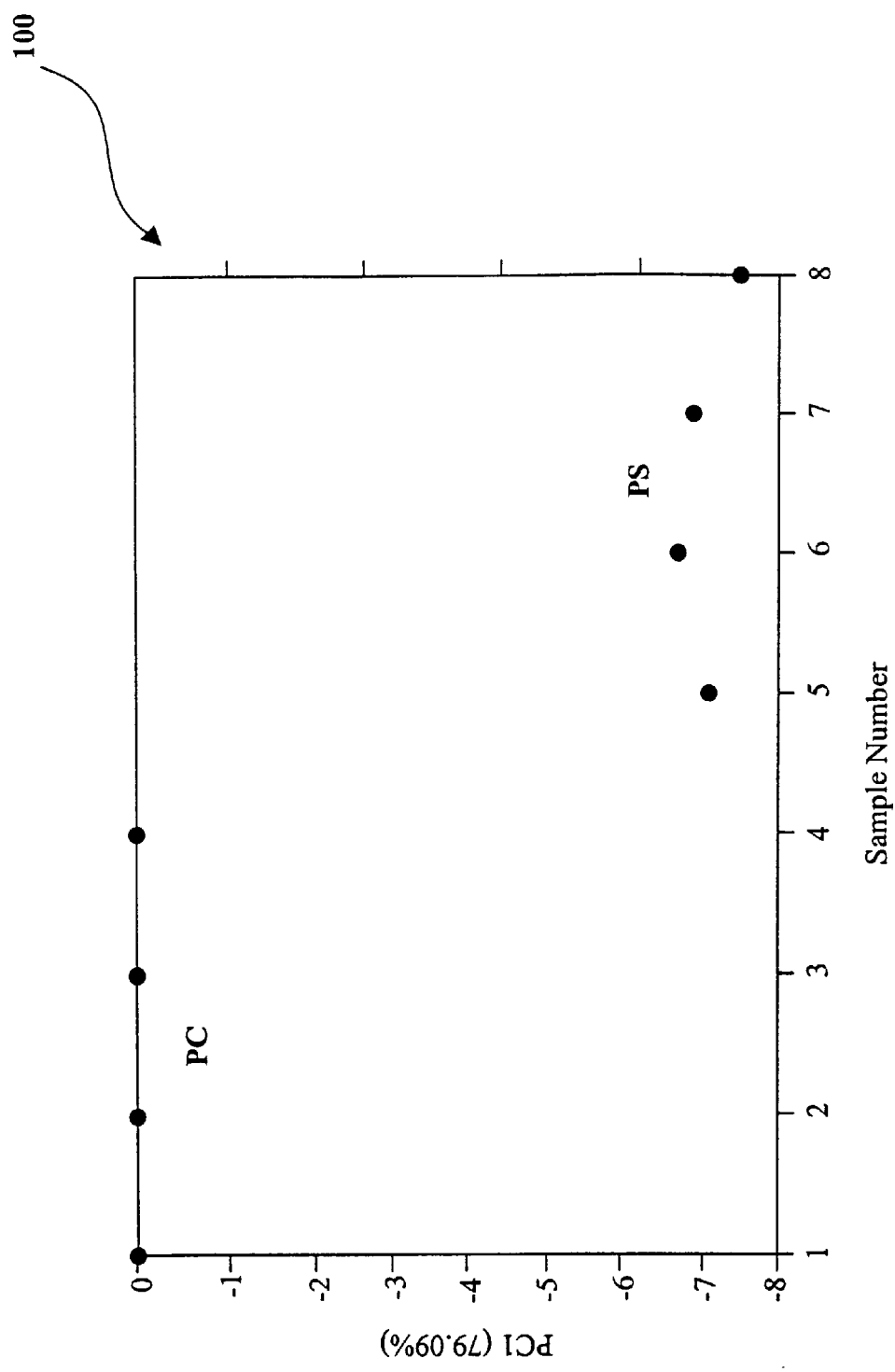
FIG. 9 is a plot illustrating the reproducibility of the analysis of different polymer test samples using the systems and methods of the present invention.

Multivariate statistical data analysis was performed to extract information about the thermal properties of the polymers from the array of full bridge devices 10 (FIG. 1). Heating/cooling cycles were performed from about 30 degrees C. to about 180 degrees C. to include the possible glass transition temperatures of the polymers. Multivariate statistical data analysis permitted the determination of the glass transition temperatures simultaneously and continuously from all channels of the array with an improved capability to identify abnormalities in sensor response. In addition, the application of Principal Components Analysis (PCA) and appropriate data pre-processing, allowed for the elimination of a plurality of variation sources affecting these determinations. Analysis of the data was performed using PCA tools available in PLS_Toolbox (Eigenvector Research, Inc., Manson, Wash.) operated with Matlab software (Mathworks Inc., Natick, Mass.). The plot 90 of FIG. 8 illustrates the results of a PCA scores plot for two polymer films evaluated in the four-channel array of full bridge devices 10 (FIG. 1). The first principal component accounts for differences in the glass transition temperatures of the two polymer films among the eight different response profiles. The second principal component describes differences in the overall intensity of the sensor response and any significant changes in the sensor response profile. Anomolous or outlier sensor response (caused by instrument malfunction or the like) are visualized in a PCA plot as a point that lies distant from other clusters on the plot. With appropriate pre-processing of the sensor response curves (e.g., min/max scaling), unwanted sources of variation that show up in the second PC may be removed. The plot 100 of FIG. 9 illustrates the reproducibility of the analysis of different polymer test samples after pre-processing of the data followed by PCA.

It is apparent that there has been provided, in accordance with the present invention, systems and methods for analyzing the thermal properties of combinatorial materials. While the present invention has been particularly shown and described in conjunction with examples and preferred embodiments thereof, it will be appreciated that variations in and modifications to the present invention may be effected by persons of ordinary skill in the art without departing from the spirit or scope of the invention. It is to be understood that the principles described herein apply in a similar manner, where applicable, to all such examples and embodiments.

What is claimed is:

1. A system operable for analyzing a viscoelastic property of a combinatorial library of materials, the system comprising:

a plurality of full bridge devices operable for measuring an environment-modulated elongation property of each of a plurality of combinatorial materials, wherein each of the plurality of combinatorial materials is disposed on a surface of the plurality of full bridge devices; and a mathematical algorithm operable for equating the environment-modulated elongation property of the combinatorial materials with a viscoelastic property of the combinatorial materials, wherein the mathematical algorithm comprises at least one of a multivariate statistical data analysis technique and a visualization algorithm.

2. The system of claim 1, wherein each of the plurality of full bridge devices comprises a plurality of strain gauges operable for measuring the environment-modulated elongation property of the combinatorial materials.

3. The system of claim 1, wherein the mathematical algorithm further comprises a Principal Components Analysis (PCA) technique.

4. The system of claim 1, wherein the mathematical algorithm is disposed within a computer.

5. The system of claim 1, further comprising a heating/cooling device operable for heating/cooling the plurality of full bridge devices simultaneously.

6. The system of claim 1, wherein each of the plurality of combinatorial materials comprises a combinatorial material selected from the group consisting of a polymer and a polymer film.

7. The system of claim 1, wherein the system is operable for analyzing the viscoelastic property of each member of a combinatorial library of materials simultaneously.

8. The system of claim 1, wherein the viscoelastic property analyzed comprises a viscoelastic property selected from the group consisting of glass transition temperature, vapor sorption, chemical resistance, weatherability, and oxidative stability.

9. A system operable for analyzing a thermal property of a combinatorial library of materials, the system comprising:
    a plurality of full bridge devices operable for measuring a temperature-modulated elongation property of each of a plurality of combinatorial materials, wherein each of the plurality of full bridge devices comprises a plurality of strain gauges operable for measuring the temperature-modulated elongation property of each of the plurality of combinatorial materials and wherein each of the plurality of combinatorial materials is disposed on a surface of the plurality of full bridge devices;
    a computer; and
    a mathematical algorithm disposed within the computer, the mathematical algorithm operable for equating the temperature-modulated elongation property of the combinatorial materials with a thermal property of the combinatorial materials wherein the mathematical algorithm comprises at least one of a multivariate statistical data analysis technique and a visualization algorithm.

10. The system of claim 9, wherein the mathematical algorithm further comprises a Principal Components Analysis (PCA) technique.

11. The system of claim 9, further comprising a heating/cooling device operable for heating/cooling the plurality of full bridge devices simultaneously.

12. The system of claim 9, wherein each of the plurality of combinatorial materials comprises a combinatorial material selected from the group consisting of a polymer and a polymer film.

13. The system of claim 9, wherein the system is operable for analyzing the thermal property of each member of a combinatorial library of materials simultaneously.

14. A method for analyzing a viscoelastic property of a combinatorial library of materials, the method comprising:
    providing a plurality of full bridge devices operable for measuring an environment-modulated elongation property of each of a plurality of combinatorial materials;
    disposing the combinatorial materials on a surface of the plurality of full bridge devices;
    measuring the environment-modulated elongation property of the combinatorial materials;
    providing a mathematical algorithm operable for equating the environment-modulated elongation property of the combinatorial materials with a viscoelastic property of the combinatorial materials, wherein providing the mathematical algorithm comprises providing at least one of a multivariate statistical data analysis technique and a visualization algorithm; and
    equating the environment-modulated elongation property of the combinatorial materials with the visco elastic property of the combinatorial materials.

15. The method of claim 14, wherein providing the plurality of full bridge devices comprises providing a plurality of strain gauges operable for measuring the environment-modulated elongation property of the combinatorial materials.

16. The method of claim 14, wherein providing the mathematical algorithm further comprises providing a Principal Components Analysis (PCA) technique.

17. The method of claim 14, further comprising providing a heating/cooling device operable for heating/cooling the plurality of full bridge devices simultaneously.

18. The method of claim 17, further comprising heating/cooling the plurality of full bridge devices simultaneously.

19. The method of claim 14, wherein each of the plurality of combinatorial materials comprises a combinatorial material selected from the group consisting of a polymer and a polymer film.

20. The method of claim 14, wherein the viscoelastic property analyzed comprises a viscoelastic property selected from the group consisting of glass transition temperature, vapor sorption, chemical resistance, weatherability, and oxidative stability.

21. A method for analyzing a thermal property of a combinatorial library of materials, the method comprising:
    providing a plurality of full bridge devices operable for measuring a temperature-modulated elongation property of each of a plurality of combinatorial materials, wherein each of the plurality of full bridge devices comprises a plurality of strain gauges operable for measuring the temperature-modulated elongation property of each of the plurality of combinatorial materials;
    disposing the combinatorial materials on a surface of the plurality of full bridge devices;
    measuring the temperature-modulated elongation property of the combinatorial materials;
    providing a mathematical algorithm operable for equating the temperature-modulated elongation property of the combinatorial materials with a thermal property of the combinatorial materials, wherein providing the mathematical algorithm comprises providing at least one of a multivariate statistical data analysis technique and a visualization algorithm; and equating the temperature-modulated elongation property of the combinatorial materials with the thermal property of the combinatorial materials.

22. The method of claim 21, wherein providing the mathematical algorithm further comprises providing a Principal Components Analysis (PCA) technique.

23. The method of claim 21, further comprising providing a heating/cooling device operable for heating/cooling the plurality of full bridge devices simultaneously.

24. The method of claim 23, further comprising heating/cooling the plurality of full bridge devices simultaneously.

25. The method of claim 21, wherein each of the plurality of combinatorial materials is comprises a combinatorial material selected from the group consisting of a polymer and a polymer film.

* * * * *